United States Patent [19]
Huang et al.

[11] Patent Number: 5,712,172
[45] Date of Patent: Jan. 27, 1998

[54] ONE STEP IMMUNOCHROMATOGRAPHIC DEVICE AND METHOD OF USE

[75] Inventors: Ching Huang, Chula Vista; Eugene Fan, La Jolla, both of Calif.

[73] Assignee: Wyntek Diagnostics, Inc., San Diego, Calif.

[21] Appl. No.: 444,238

[22] Filed: Apr. 18, 1995

[51] Int. Cl.⁶ .................. G01N 33/543; G01N 33/558
[52] U.S. Cl. ............... 436/518; 422/56; 422/57; 422/58; 435/287.1; 435/287.2; 435/287.7; 435/287.9; 435/805; 435/810; 435/967; 435/970; 435/971; 436/169; 436/510; 436/514; 436/523; 436/525; 436/531; 436/534; 436/805; 436/810; 436/814; 436/818; 436/65
[58] Field of Search .............. 422/56–58; 435/287.1, 435/287.2, 287.7, 287.9, 805, 810, 967, 970, 971; 436/169, 510, 514, 518, 523, 525, 531, 534, 805, 810, 65, 814, 818

[56] References Cited

U.S. PATENT DOCUMENTS

| | | | |
|---|---|---|---|
| 4,235,601 | 11/1980 | Deutsch et al. | 422/56 |
| 5,160,701 | 11/1992 | Brown, III et al. | 422/56 |
| 5,354,692 | 10/1994 | Yang et al. | 436/514 |
| 5,356,785 | 10/1994 | McMahon et al. | 435/7.92 |
| 5,384,264 | 1/1995 | Chen et al. | 422/56 |
| 5,409,664 | 4/1995 | Allen | 422/56 |
| 5,424,220 | 6/1995 | Goerlach-Graw et al. | 436/568 |
| 5,541,059 | 7/1996 | Chu | 435/5 |
| 5,559,041 | 9/1996 | Kang et al. | 436/518 |

*Primary Examiner*—Christopher L. Chin
*Attorney, Agent, or Firm*—Lyon & Lyon LLP

[57] ABSTRACT

This invention relates to a lateral flow immunochromatographic assay device without a plastic housing. The assay includes a sample receiving region, analyte detection region and end region all made of porous material and capable of lateral flow. The analyte detection region includes labeling reagents, a capture reagent and a control reagent. The back of the porous material is laminated with a semi-rigid material with adequate mechanical strength. The top is partially covered with a thin plastic material so as to leave a portion of the sample receiving region exposed for sample application.

17 Claims, 3 Drawing Sheets

ONE STEP IMMUNOCHROMATOGRAPHIC
DEVICE AND METHOD OF USE

BACKGROUND OF THE INVENTION

This invention relates to immunological methods and devices for detecting analytes in biological samples.

Numerous approaches have been developed for detection of a given analyte in a biological sample. Typical of these methods are the so called "dipstick," "lateral flow" and "flow-through" devices and methods. The dipstick generally uses a plastic strip with a reagent-containing matrix layered thereon. A test sample is applied to the device, and the presence of the analyte is indicated by a visually detectable signal such as a color-forming reaction. The flow-through device generally uses a porous material with a reagent-containing matrix layered thereon or incorporated therein. Test sample is applied to and flows through the porous material, and analyte in the sample reacts with the reagent(s) to produce a detectable signal on the porous material. These devices are generally encased in a plastic housing or casing with calibrations to aid in the detection of the particular analyte.

Lateral flow assays also utilize a porous membrane for performing analyte detection. Instead of drawing the sample through the membrane perpendicularly, however, the sample is permitted to flow laterally from an application zone to a reaction zone on the membrane surface. The capture reagent is present in the reaction zone, and the captured analyte can be detected by a variety of protocols, including direct visualization of visible moieties associated with the captured analyte.

For example, Hochstrasser, U.S. Pat. No. 4,059,407, discloses a dipstick device which can be immersed in a biological fluid to semi-quantitate analyte in the fluid. Semi-quantitation of the analyte is accomplished by using a series of reagent-containing pads wherein each pad in the series will produce a detectable color (i.e., a positive result) in the presence of an increasing amount of analyte.

Deutsch et al. describe a quantitative chromatographic test strip device in U.S. Pat. Nos. 4,094,647, 4,235,601 and 4,361,537. The device comprises a material capable of transporting a solution by capillary action, i.e., wicking. Different areas or zones in the strip contain the reagents needed to produce a detectable signal as the analyte is transported to or through such zones. The device is suited for both chemical assays and binding assays which are typified by the binding reaction between an antigen and its complementary antibody.

Many variations on the Deutsch et al. device have also been disclosed. For example, Tom et al., U.S. Pat. No. 4,366,241 discloses a bibulous strip with an immunosorbing zone to which the test sample is applied. Grubb et al., U.S. Pat. No. 4,168,146 describes the use of a porous test strip material to which is covalently bound an antigen-specific antibody. In performance of an assay, the test strip is immersed in a solution suspected of containing an antigen, and capillary migration of the solution up the test strip is allowed to occur. As the antigen moves up the test strip it binds to the immobilized antigen-specific antibody. The presence of antigen is then determined by wetting the strip with a second antigen-specific antibody to which a fluorescent or enzyme label is covalently bound. Quantitative testing can be achieved by measuring the length of the strip that contains bound antigen.

Numerous variations of the above test strip are disclosed in U.S. Pat. No. 4,435,504 which employs a two enzyme indicator system. U.S. Pat. No. 4,594,327 discloses the addition of a binding agent to whole blood samples which causes the red blood cells to aggregate at the area of the strip adjacent to the air/liquid interface. In addition, U.S. Pat. No. 4,757,004 discloses a means for controlling the shape of the fluid front migrating along the test strip. Also of interest are U.S. Pat. Nos. 4,298,688, 4,517,288 and 4,740,468 which describe sheet-like diagnostic devices comprising one or several strips, arranged behind one another, having zones situated one behind another. Each zone is readily accessible from above and below for the addition of reagents. Such devices can quantitatively determine the amount of an analyte.

In addition, European Publication No. 323,605 discloses an assay device using chromatographic material wherein the test sample can travel from one end to the other by capillary action. The chromatographic material contains an immobilized capture reagent capable of binding to the analyte. The application pad receives the test sample and contains a diffusive indicator reagent capable of migrating from the application pad to the chromatographic material. The indicator reagent is capable of binding to the analyte or the capture reagent. The binding of the indicator reagent results in a detectable signal.

Procedures using chromogenic and fluorescent dyes as labels in biological assay procedures are also known. Typical assay protocols call for direct or indirect binding of a dye label to an analyte or analyte analog in a biological sample, where the presence or absence of the dye at a particular stage of the assay can be determined visually and related to the amount of analyte initially present in the sample. A wide variety of specific assay protocols exist.

A number of those assays utilize naturally colored or dyed particles as a label, where the particles are bound to an antibody or other specific binding substance. Suggested particles include dyed latex beads, dye imbibed liposomes, erythrocytes, metal sols, and the like. The colored particle in such complexes can serve as a visible marker, where separation, capture, or aggregation of the particles is mediated through binding of the antibody or other specific binding substance. The amount of label thus segregated in a particular assay step is related to the amount of analyte initially present in the sample.

For example, U.S. Pat. No. 4,943,522 describes a solid phase lateral flow assay using erythrocytes as a label. U.S. Pat. No. 4,863,875 describes compositions comprising at least ten dye molecules or monomers covalently attached to an antibody through an isocyanate group on the dye. U.S. Pat. No. 4,703,017 describes a solid phase assay device which relies on specific binding of a ligand-label conjugate on a solid support, where the label is disclosed as a particle, such as a liposome, or polymer microcapsule. U.S. Pat. No. 4,608,246 describes assays for typing blood which employ erythrocytes as a labeling agent. U.S. Pat. No. 4,452,886 describes the covalent attachment of photon absorbing or emitting polymers to proteins, such as antibodies and antigens. U.S. Pat. No. 4,373,932 describes labeling of a ligand with an aqueous dispersion of a hydrophobic dye or pigment, or a polymer nuclei coated with such a dye or pigment. U.S. Pat. No. 4,313,734 describes methods of detecting sample analytes by the determination of the metallic label content in the sample. U.S. Pat. No. 4,169,138 describes immunoassays which employ visible particles including undyed microorganisms, bound to polymers which may be of microbial origin.

Other lateral flow protocols include U.S. Pat. No. 4,943,522 directed to a lateral flow device which relies on a nonbibulous support to conduct liquids from one portion of the device to another. PCT Publication WO 92/12428, which is related to the above patent, represents an improvement on that method and device wherein nonbibulous lateral flow is used to conduct visible moieties, especially labeled particles, e.g., dyed latex, red blood cells or liposomes capable of reacting with analyte or a competitor thereto into a capture zone for detection, using a bibulous support made nonbibulous by treatment with a blocking agent. The result is a one-step assay which can be conducted in a very short period of time (typically, within 60 seconds), and wherein the readout is usually available instantaneously upon the sample contacting a capture zone.

Other disclosures of lateral flow assays have also appeared. For example, U.S. Pat. No. 4,861,711 describes a lateral flow assay wherein all components needed for the detection of an analyte are embedded in a single sheet. The lateral flow is referred to as chromatographic behavior. This patent discloses the use of enzyme antibody conjugates and substrates, each separately held in absorbent pads. European Patent Application 306,772 describes a lateral flow device which comprises a chromatographic medium wherein the zone for application of sample and the reaction zone with an immobilized reagent capable of binding the analyte or a label-specific binding material are separated. British Application No. 2,204,398 describes a lateral flow device wherein sample applied to the device picks up labeled reagent and permeates into a detection zone. Labels include gold sols and colored particles. U.S. Pat. No. 4,168,146 describes lateral flow through a test strip which determines the presence of an analyte by addition of a suitable color indicator.

European Application No. 276,152 describes a bibulous matrix lateral flow device which operates on two separate planes. U.S. Pat. No. 4,857,453 describes a device wherein reagents are supplied in breakable containers which are integral to the device. European Patent No. 158,746 and U.S. Pat. No. 4,775,636 describe the use of metal sols as visible detecting labels for specific binding assays.

Furthermore, U.S. Pat. No. 4,703,017, describes test strip devices wherein binders for an analyte and/or a visible tracer are applied to defined areas of a solid support by adsorption or covalent coupling. After application of the binder to one or more test areas of the substrate, the residual binding capacity of the test substrate is saturated or blocked by treatment with one or more types of proteins which do not specifically bind the materials to be employed in the assay. The tracer, when bound under assay conditions to the binder or to the analyte bound to the binder, is visible on the support without further treatment. The test strip is contacted and incubated with a sample containing (or suspected of containing) analyte. A sample strip may be provided with a plurality of test areas. U.S. Pat. No. 4,855,240 describes an assay wherein a sample and a tracer as described in U.S. Pat. No. 4,703,017 are applied at disparate locations on a flat lateral flow device. As noted before, the above devices are contained within a plastic housing or casing.

SUMMARY OF THE INVENTION

Applicants have determined that it is useful to construct the lateral flow immunochromatographic assay devices of the present invention without plastic casings. Specifically, a porous material is laminated to provide an end product with an adequate mechanical strength, i.e., a particular thickness and strength characteristic for support. In addition, added strength is also achieved by a plastic cover used on top of the porous material. This device provides a simple, convenient, rapid and direct sample application method to the user with a cost effective design. Because no plastic casing is used, this invention also provides a more environmental friendly device. This device can then be used to detect various analytes in a liquid sample.

Taking advantage of the test device of the present method, the device can be utilized with a method for detection of analytes directly from a biological sample, such as urine. In particular, the invention can be used to detect the presence or absence of human chorionic gonadotropin ("hCG"). Such detection is useful, in determining a positive or negative pregnancy in women.

The first aspect of the present invention features an immunochromatographic assay device for the detection of the presence or absence of an analyte in a liquid sample. The immunochromatographic assay device comprises a separated sample receiving region which is made of a porous material. The porous material conducts lateral flow of the liquid sample. The sample receiving region is in contact with a separate analyte detection region. Lateral flow of the liquid sample will continue from the sample receiving region to the analyte detection region. The analyte detection region contains a porous material which conducts lateral flow of the liquid sample. The analyte detection region contains mobile labeling reagents located at a discrete situs. It also contains an immobile capture reagent at a discrete situs. In addition, it also contains a control reagent at a discrete control situs. The analyte detection region is also in lateral flow contact with the end flow region. The end flow region contains a porous material which conducts lateral flow of the liquid sample. It is capable of absorbing excess liquid sample.

In the above aspect, the one labeling reagent is capable of forming a complex with the analyte. The second labeling reagent is mobile but does not form a complex with either the analyte or the capture reagent. The capture reagent is capable of binding the analyte labeling reagent complex. The control reagent is capable of binding the second labeling reagent. In addition, the porous materials in the above aspect are laminated with one continuous or separate semi-rigid material of at least 0.005 inches thick. The laminate covers the back only and provides adequate mechanical strength to the device, i.e., it provides support and strength characteristics to the porous material and overall device. The front of the porous materials are partially covered with a plastic material so as to leave a portion of the sample receiving region exposed for sample application. The capture situs and the control situs can be seen through the plastic cover.

The term "analyte" as used herein refers to a compound or composition to be detected or measured in the test sample. The analyte will have at least one epitope that an antibody or an immunological reactive fragment thereof can recognize. Analyte can include any antigenic substances, haptens, antibodies and combinations thereof. The analyte of interest in an assay can be, for example, a protein, a peptide, an amino acid, a nucleic acid, a hormone, asteroid, a vitamin, a pathogenic microorganism for which polyclonal and/or monoclonal antibodies can be produced, a natural or synthetic chemical substance, a contaminant, a drug including those administered for therapeutic purposes as well as those administered for illicit purposes, and metabolites of or antibodies to any of the above substances. One preferred example of a hormone suitable for detection is human chorionic gonadotropin ("hCG").

The term "sample" as used herein refers to any biological sample that could contain an analyte for detection. Preferably the biological sample is in liquid form or can be changed into a liquid form. Preferably, the sample is a urine sample.

As used herein, the term "sample receiving region" means the portion of the assay device which is in direct contact with the liquid sample, i.e., it receives the sample to be tested for the analyte in question. The liquid sample can then migrate, through lateral flow, from the sample receiving region towards the end flow region. The sample receiving region is in lateral flow contact with the analyte detection region. This could either be an overlap or end-to-end connection. The analyte in the sample must be capable of migrating, through lateral flow, with the liquid sample. The sample receiving region is made of porous material, usually porous paper.

As used herein, the term "porous material" refers to any material capable of providing lateral flow. This would include material such as nitrocellulose, nitrocellulose blends with polyester or cellulose, untreated paper, porous paper, rayon, glass fiber, acrylonitrile copolymer or nylon. One skilled in the art will be aware of other porous materials that allow lateral flow. The term "lateral flow" refers to liquid flow in which all of the dissolved of dispersed components of the liquid are carried at substantially equal rates and with relatively unimpaired flow laterally through the material, as opposed to preferential retention of one or more components as would occur, e.g., in materials capable of adsorbing or imbibing one or more components.

The term "mobile" as referred to herein means diffusively or non-diffusively attached, or impregnated. The reagents which are mobile are capable of dispersing with the liquid sample and carried by the liquid sample in the lateral flow. The term "immobile" as used herein refers to reagents which are attached to the support such that lateral flow of the liquid sample does not affect the placement of the immobile particle in the discrete region of the porous material. Such attachment can be through covalent or ionic means. Those skilled in the art will be aware of means of attachment to immobilize various particles.

The term "labeling reagent" as used herein refers to any particle, protein or molecule which recognizes or binds to the analyte in question or a particle, molecule, protein which does not recognize, or bind to the analyte and has attached conjugated or bound to it, either chemically, covalently or noncovalently, ionicly or nonionicly any substance capable of producing a signal that is detectable by visual or instrumental means. Such labels producing a signal would include chromogens, catalysts, fluorescent compounds, colloidal metallic and nonmetallic particles, dye particles, enzymes or substrates, organic polymers, latex particles, liposomes with signal producing substances and the like. The particle or molecule recognizing the analyte can be either natural or non-natural, preferable monoclonal or polyclonal antibody. One labeling reagent can be a monoclonal antibody to the β-epitope of hCG and bound to Blue latex and another labeling reagent can be BSA bound to red color latex.

The term "capture reagent" as used herein refers to any particle or molecule which recognizes or binds the analyte in question. The capture reagent is capable of forming a binding complex with the labeling reagent that has binded to the analyte in the sample. The capture reagent is immobilized to the porous material of the analyte detection region. The capture reagent is not affected by the lateral flow of the liquid sample due to the immobilization to the porous material. The particle of molecule can be natural, or non-natural, i.e., synthetic. Once the capture reagent binds the analyte-labeling reagent complex it prevents the analyte-labeling reagent from continuing with the lateral flow of the liquid sample.

The term "control reagent" as used herein refers to any particle or molecule which is capable of binding the labeling reagent which does not recognize or bind the analyte of question in the sample. For example, the labeling reagent may be BSA conjugated to a red latex. The control reagent would be a particle or molecule which recognizes or binds the BSA conjugated red latex labeling reagent. Preferably, the control reagent would be a monoclonal or polyclonal antibody which recognizes BSA. The control reagent is immobilized to the porous material. Once it binds the labeling reagent it immobilizes the labeling reagent and prevents it from continuing lateral flow with the liquid sample. Just as the capture reagent is immobilized in a discrete situs on the porous material of the analyte detection region, the control reagent is also immobilized in a discrete situs on the porous material of the analyte detection region.

The term "analyte detection region" as used herein refers to the portion of the assay device which is in lateral flow contact with the porous material of the sample receiving region and the end flow region. The contact can be an overlap or end-to-end connection. The analyte in the sample must be capable of migrating through lateral flow with the liquid sample. The analyte detection region is made of a porous material just as the sample receiving region is. Preferably, the analyte detection region is made of nitrocellulose. The sample receiving region, the analyte detection region and the end flow region can be made of different material. The analyte detection region can contain the mobile labeling reagents, the immobile capture reagent and the immobile control reagent. In other embodiments the analyte detection region contains only the immobilized control and capture reagents.

The term "discrete capture situs" or "discrete control situs" as used herein refers to a defined area in which either the labeling reagents, the capture reagent or the control reagent are impregnated (for the labeling reagents) or immobilized (for the control or capture reagents) to the porous material. The discrete capture situs of the control or the capture reagents provide a discrete visible line from which to view the results of the test. For example, if the one labeling reagent is analyte bound to anti-analyte conjugated to Blue latex, then a discrete blue line will appear at the discrete capture situs if the capture reagent binds and immobilizes the analyte labeling reagent complex. If the second labeling reagent is BSA conjugated to red latex then a discrete line will form at the discrete control situs if the control reagent immobilized the BSA red latex labeling reagent.

The term "end flow region" as used herein refers to the portion of the assay device which is in lateral flow contact with the analyte detection region. The liquid sample migrates to the end flow region. It is capable of absorbing excess liquid sample. The contact with the analyte detection region can be either by overlap or end-to-end connection. This region is made of porous material, usually porous paper.

The term "semi-rigid" as used herein refers to the material used to support the porous material of the device. This can be one continuous piece of laminate or separate pieces. The laminate is preferably vinyl but one skilled in the art will recognize that numerous materials can be used to provide the semi-rigid support. The semi-rigid material must at least be of 0.005 inches thick in order to produce the desired adequate mechanical strength or support for the device to function effectively.

The term "adequate mechanical strength" as used herein refers to a desired support to the assay device so as to function properly. This would include a desired thickness to the backing material, as well as bending characteristics when using weighted standards or bending characteristics when using water flow measurements. The adequate mechanical strength is the support achieved for the entire assembled assay device so as to function properly in the collection and analysis of the analyte in the liquid sample. The minimum adequate mechanical strength is a thickness of 0.005 inches thick with a 10 mm bending measurement using a 10 g weight or 5 mm bending measurement using water flow. Such strength characteristics or measurements provide the minimum standard necessary for proper function of the device. The preferred adequate mechanical strength is 0.02 inches thick, 1 mm bending using the 10 g weight measurement or 5 mm bending using the water flow measurements. Such preferred measurements provided sufficient strength and support to the porous material and assay device that no bending is obtained when the assay is used with a urine stream or water flow.

The term "plastic material," or "plastic cover," or "cover" as used herein refers to any plastic material which can cover the porous material of the device. Preferably, this is mylar, however, those skilled in the art will know of various materials that can be used for such purposes. The cover can be one continuous plastic or separate pieces as shown in the figures. It must allow the discrete control and discrete capture situses to be viewed. Thus, if the cover is clear then the result can be viewed through the clear cover. If the cover is not clear, then a window, gap or hole must be used so the results can be viewed. In addition, the cover must leave a portion of the sample receiving region exposed so the sample can be applied to the receiving region.

Other features and advantages of the invention will be apparent from the following detailed description of the invention in conjunction with the accompanying drawings and from the claims.

DESCRIPTION OF THE DRAWINGS

The drawings are not necessarily to scale, and certain features of the invention may be exaggerated in scale and shown in schematic form in the interest of clarity and conciseness.

DETAILED DESCRIPTION OF THE INVENTION

The following are examples of the immunochromatographic assay device of the present invention. These examples are offered by way of illustration and are not intended to limit the invention in any manner.

Figure 1:
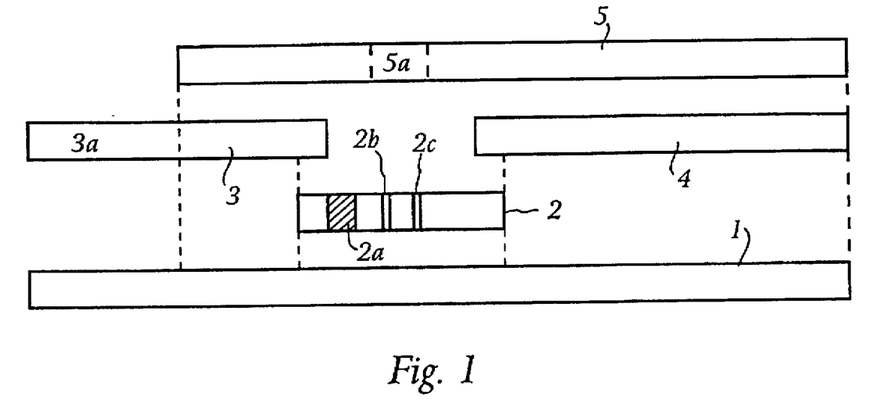
FIG. 1 illustrates an expanded perspective view of the immunochromatographic elements assembled into a test device according to the present invention.

FIG. 1 depicts an exemplary embodiment of the invention. A series of porous material pieces (2), preferably nitrocellulose material, and (3) and (4), both preferably porous paper material, are laminated to an elongated strip of a semi-rigid material (1), such as vinyl and the like. The semi-rigid material is required to have an adequate mechanical strength (as defined above and discussed below) in order to act as the main support for the device. The separate sample receiving region (3) is a porous material, usually paper, and is in direct lateral flow contact with the analyte detection region. The separate analyte detection region (2) is in direct lateral flow contact with the separate end flow region (4). The assembly is such that there is end-to-end contact of each region or overlaps sufficiently to provide continuous wicking action (i.e., continuous lateral flow). A strip of plastic material (5), preferably clear mylar, is covered on top of the device except leaving a portion of the front pad exposed for sample application. Portion (5a) can be a window or clear so as to permit viewing of the capture and control discrete situses, i.e., to permit viewing of the results.

In one aspect, analyte detection region (2) of the immunochromatographic assay device contains two mobile labeling reagents in a discrete situs (2a), an immobile capture reagent in a discrete situs (2b) and an immobile control reagent at a discrete situs (2b). The mobile label reagents consist of a first reagent, preferably a monoclonal or polyclonal antibody, that specifically binds the analyte to be detected. Attached to the antibody, either covalently or noncovalently, is a substance or particle capable of producing a signal detected visually. Such labeled particles used can be colloidal gold, dye sols, colored latex and the like. Preferably, the label is latex (Blue). One skilled in the art will recognize suitable labeling particles. The second mobile labeling reagent is a particle or molecule which does not recognize the analyte and is conjugated to a substance or particle capable of producing a signal. Preferably, the second labeling reagent is BSA conjugated to latex (Red).

In an assay, the exposed sample receiving region (3a) of the assay device is directly placed into a sample, for example, a urine stream. The sample flows laterally along the porous material region (2) by capillary action and migrates the labeled particles (2a). The presence and/or the amount of analyte in the sample may then be determined by the visibility of a line (2b) formed by the capture reagent specific for the analyte-label reagent conjugate. The appearance of a second line (2c) may be utilized as a built-in control feature. This control feature recognizes the second labeling reagent, e.g., BSA-Red latex. If the reagents or assay is working properly, then a red line will appear at (2b) the discrete control situs. The results of an assay can then be observed through a viewing window (5a) covered by clear mylar.

Figure 2:
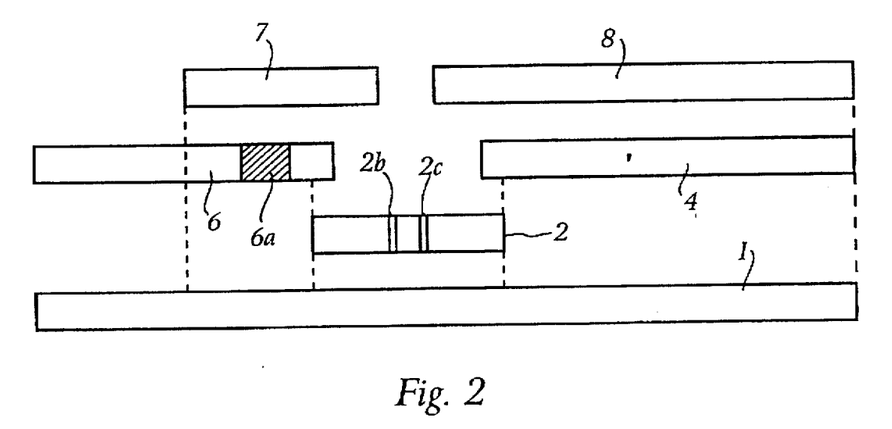
FIG. 2 illustrates an expanded perspective view of the immunochromatographic elements of the present invention with an alternative placement of labeled color particles and an alternative layout of the upper covering.

In an alternative design, as illustrated in FIG. 2, the labeled particles (6a) can be impregnated near one end of the sample receiving region (6). FIG. 2 also shows an alternative layout of the upper covering, in which a front piece (7) covers the labeled particles area (6) and an end piece (8) covers the end flow region whereas leaving a section of analyte detecting region (2) open for viewing the test results at (2b) and (2c).

Figure 3:
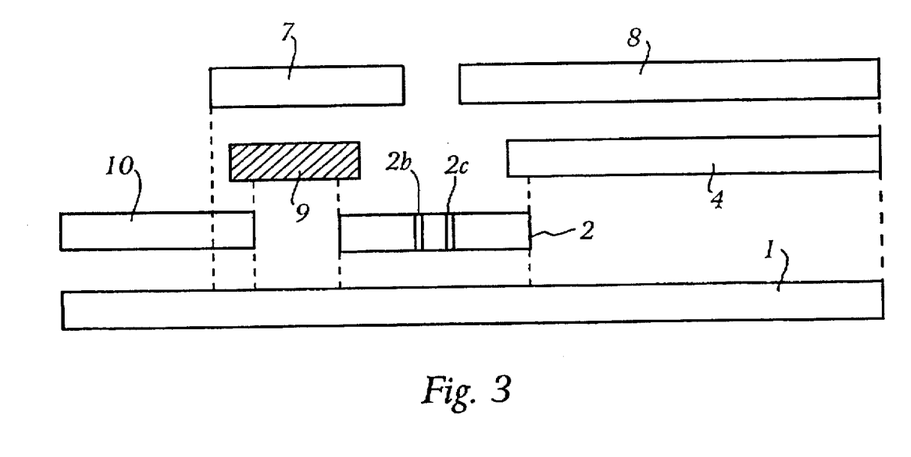
FIG. 3 illustrates an expanded perspective view of the immunochromatographic elements of the present invention with another alternative layout of the labeled color particles.

In another alternative design, as illustrated in FIG. 3, a separate piece of absorbent material (9), containing labeled particles is placed between the sample receiving region (10) and the analyte detection region (2). Both the layouts in FIGS. 2 and 3 require lateral flow of the porous membranes. Overlap or end-to-end connection can be used as long as lateral flow occurs.

Figure 4:
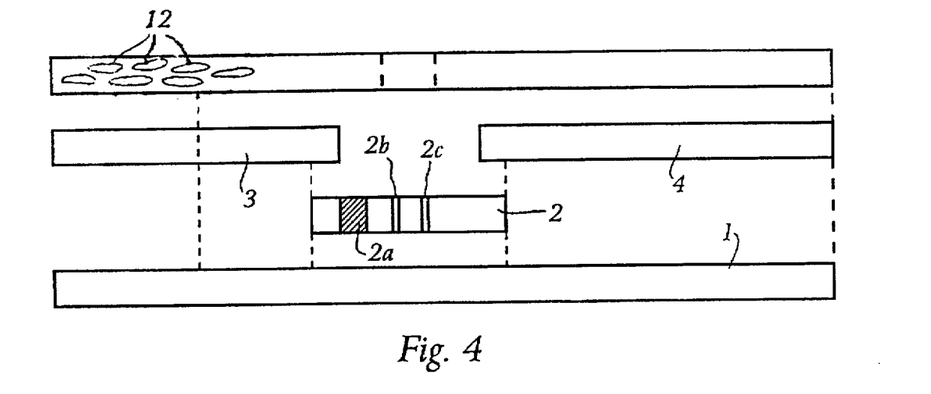
FIG. 4 illustrates an expanded perspective view of the immunochromatographic elements of the present invention with an alternative layout of the upper covering.

In yet another alternative design, as illustrated in FIG. 4, the plastic cover (11) is extended to cover the entire sample receiving region (3) with openings or holes exposed (12) for receiving the sample. This design also allows for viewing the analyte detection region (2b) and (2c).

Figure 6A:
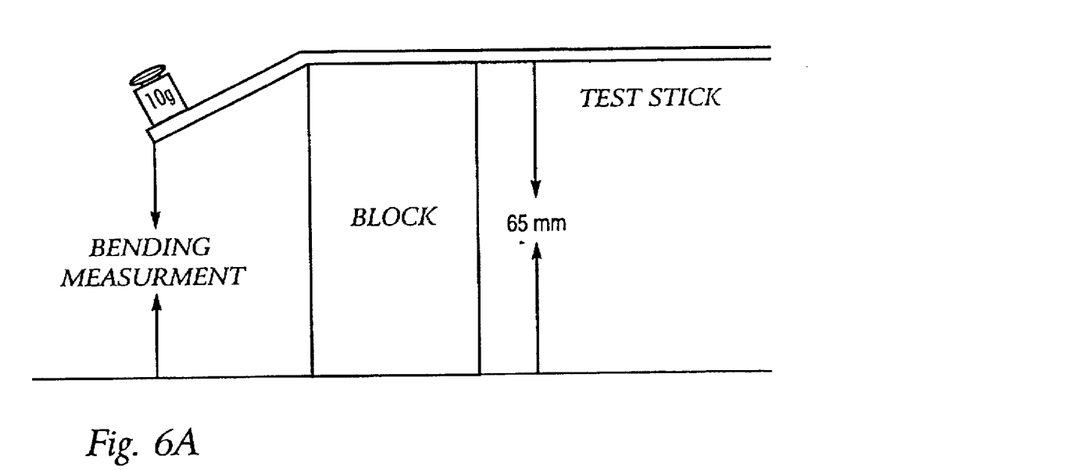
FIGS. 6a and 6b illustrate a method of measuring bending of a stick device.
Figure 6B:
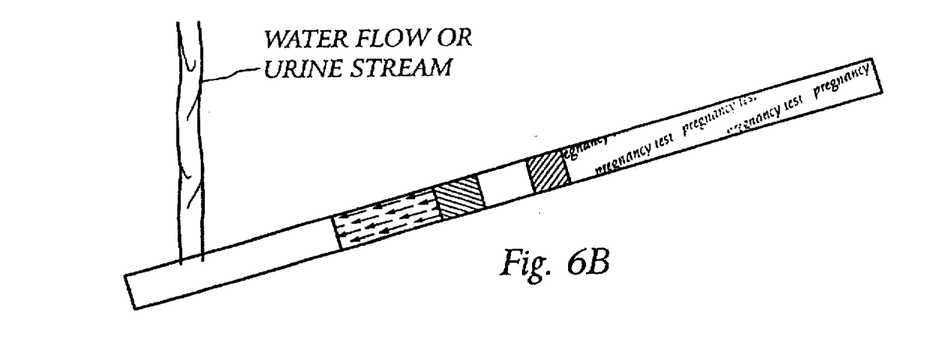

The invention as described above provides a method for direct sample application to the device without the need of an additional specimen collection procedure. This provides an advantage of a more rapid and convenient test procedure to the user. The selection of proper materials with adequate mechanical strength (as defined above and described below) as the supportive backing and the sample receiving region for the device is important. Undesirable bending of the assay on the edge of the sample receiving region. The bending distance is then measured as the difference between the height of the block, 65 mm, and the height of the edge of the sample receiving region with weight. The larger the difference, the greater the bending. In the second method, the 10 g weight attachment is replaced by 10 seconds of tap water flow (see FIG. 6b) simulating urine stream and then the same type of the measurement is performed as in the first method. The results shows that the thicker the backing, the less the bending, and hence more favorable results. Again, this demonstrates that in an assay device without a rigid plastic casing support, adequate thickness of the backing material or the adequate mechanical strength of the entire assembly is critical for the device to function properly and collect sample directly from urine stream.

TABLE 1

| Material | Thickness | Bending Measurement Using 10 g Weight | Bending Measurement Using Water Flow | Integrity of Stick after Water Flow Assay |
|---|---|---|---|---|
| Mylar | 0.003 inch | 17 mm bending | 12 mm bending | Major bending; Not satisfactory |
| Mylar | 0.005 inch | 10 mm bending | 5 mm bending | Some bending; Barely adequate |
| Vinyl | 0.010 inch | 8 mm bending | 2 mm bending | Minor bending; Fairly adequate |
| Vinyl | 0.015 inch | 5 mm bending | 1 mm bending | Very minor bending; Very adequate |
| Vinyl | 0.020 inch | 1 mm bending | no measurable bending | No bending; Most preferable | device may occur if a weak backing or inadequate mechanical strength is used. For example, comparison of mylar or vinyl material with different thickness demonstrates the necessary or adequate parameters for mechanical strength (see Table 1).

The results in Table 1 are gathered from an experiment described hereinafter. Porous material of the present invention with various thickness of mylar or vinyl backing (FIGS. 1–4), were assembled according with the dimensions shown below. The porous material for the analyte detection region was nitrocellulose membrane which was laminated with 0.005 inches mylar, the sample receiving region and end flow region used cotton linter absorbent papers with 0.84 mm thickness. The plastic cover was a 0.004 inches clear mylar.

| Dimensions of the Exemplary Assay Device | |
|---|---|
| Upper Covering: | 6 mm × 98 mm |
| Lower Backing: | 6 mm × 129 mm |
| Front Pad: | 6 mm × 51 mm |
| Exposed Front Pad: | 6 mm × 31 mm |
| End Pad: | 6 mm × 59.5 mm |
| Porous Material: | 6 mm × 25.4 mm |
| Viewing Window: | 6 mm × 9 mm |

Figure 5:
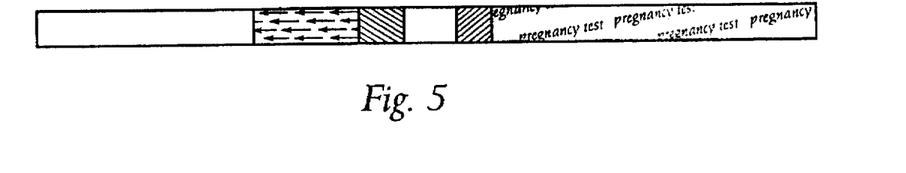
FIG. 5 illustrates a test device constructed according to the present invention having upper covering printed with product information.

(Note: Product information may be printed on the upper covering as shown in FIG. 5.)

The adequate mechanical strength of the assembled assay device is measured in two ways. In the first method (see FIG. 6a), the assay device is placed on a 65 mm height block with the exposed end of the sample receiving region facing up and sitting outside of the block. While anchoring the assay device on the block with one hand, a 10 g weight is attached In yet another aspect, the present invention comprising an immunochromatographic assay device without molded plastic casings greatly reduces the cost for manufacturing. In addition, the advantage of using a same basic design with universal applicability for different analytes also promotes the objective of inventory reduction.

Preparation of One-Step Assay for Human Chorionic Gonadotropin (HCG) in Urine

Selection of Materials

1. Analyte Detection Region: Important features of the material are its fluids wicking and protein binding abilities. Exemplary material includes nitrocellulose, nylon or the like. In a preferred embodiment of this invention, the material is nitrocellulose with or without laminated solid support such as polyester. Nitrocellulose is readily available from numerous suppliers.

2. Sample Receiving Region: Suitable materials include cotton, cellulose, mixed fibers, glass fiber and the like. For example, paper such as 470 and 740-E from Schleicher and Schuell, Keen, N.H., or D28 from Whatman, Fairfield, N.J., can be selected for its high fluid absorption and wicking speed. A more porous material such as glass fiber #66078 from Gelman Sciences, Ann Arbor, Mich., or POREX from Porex Technologies, Fairburn, Ga., is suitable for impregnating labeled particles.

3. Backing Supports: For the present invention, the preferred materials are clear mylar with thickness about 0.001 inches to 0.010 inches for the upper covering and white vinyl with thickness about 0.005 inches to 0.030 inches for the lower backing. Both the mylar and the vinyl sheets have adhesive on one side so as to attach the porous material. Materials such as mylar, polyester, and vinyl with adhesive are readily available.

4. Labeling Reagents: A chromogenic particulate such as latex, colloidal gold, selenium or the like is labeled with a suitable reagent specific for the targeted analyte. For the present invention, the preferred chromogenic particulate is latex. Latex is commercially available from a number of sources.

The monoclonal anti-β-hCG antibody can be obtained from Medix Biotech (San Carlos, Calif.), Medix Biochemica (Kauniainen, Finland), or other commercial sources. The affinity purified polyclonal anti-α-hCG antibody (rabbit) can be purchased from Bioreclamation (East Meadow, N.Y.), H.T.I. Bio-Products, Inc. (Ramona, Calif.) and other sources. As is discussed below, the capture reagent recognizes the β-epitope of hCG while the control agent recognizes the α-epitope of hCG, or vice versa.

Preparation of Latex Conjugates

The basic protocol for conjugation of protein to latex, by simple adsorption or by covalent binding, is well known in the art and is hereby incorporated by reference. For the present invention, covalent binding of anti-β-hCG antibody to blue latex and covalent binding of BSA to red latex are described hereinafter.

Blue carboxylated latex particles (0.2 to 0.5 microns) were activated with 0.2% EDAC in the presence of 0.1% sulfo-NHS in 20 mM MES buffer, pH 5.5, for 30 minutes at room temperature. The excess amount of reagents were removed by washing in an Amicon Concentrator. The activated latex particles were resuspended in 2 mM MES buffer, pH 6.5 to a concentration of 0.5%, and a ratio of 0.05 mg of monoclonal anti-HCG antibody were added to 1 mg of latex. The mixture was incubated at room temperature for 2 hours. After incubation, the conjugated latex was washed again to remove free antibody. The antibody-latex conjugate was then sonicated, filtered, and resuspended in buffer containing 20 mM Tris, pH 8.5; 20% sucrose; 0.5% casein.

The conjugation of BSA to red carboxylated latex (size of 0.2 to 0.5 microns) was essentially the same as described above except replaced the blue latex with red latex and anti-β-HCG with BSA.

Preparation of Latex Coating Solution

The blue latex solution and the red latex solution were mixed at a ratio from 5:1 to 1:1 depends upon the sensitivity of the conjugate and intensity of red control line desired. The preferable ratio is approximate 1:1. These solutions are then impregnated into the porous material using methods well known in the art, all of which are hereby incorporated by reference.

Coating of Anti-α-HCG Antibody (Capture Reagent) and Anti-BSA (Control Reagent Line) on the Discrete Situses of the Porous Material Thin lines of either antibodies were applied on the material using airbrush techniques (Iwata, model HP-BC2). The width of the lines can be 0.2 mm to 2 mm, a width of 1 mm is preferred. Such material is immobilized by techniques well known in the art, hereby incorporated by reference.

Coating of Latex Conjugate (Labeling Reagents) on the Material

Immediately after the antibodies were applied on the material. The latex solution can be applied on the material by using airbrush techniques (Iwata, model HP-BC2). The membrane strip is then dried in a force air oven at 70° C. for 45 minutes. Such application allows the labeling reagents to be mobile.

Preparation of Sample Receiving Region

In this invention, the sample receiving region not only absorbs and transports liquid sample, it also functions as a specimen collection apparatus. The front pad may further be treated with buffer containing detergents, blocking proteins and the like to facilitate movement of dried latex particles or to reduce nonspecific binding of the assay. In the case of the hCG assay, an appropriate amount of buffer solution was dispensed to the front pad, dried, and then assembled into the assay device. Specifically, 0.4 mL of buffer solution containing 4% zwittergent 3–12, 1% rabbit gamma globulin, 1% casein and 200 mM Tris, pH 8.5 were applied on 200 mm long strip of front pad at it's edge. The sample receiving region is then dried in a forced air oven at 70° C. for 15 minutes.

Assembly of the Assay Device

Figure 7:
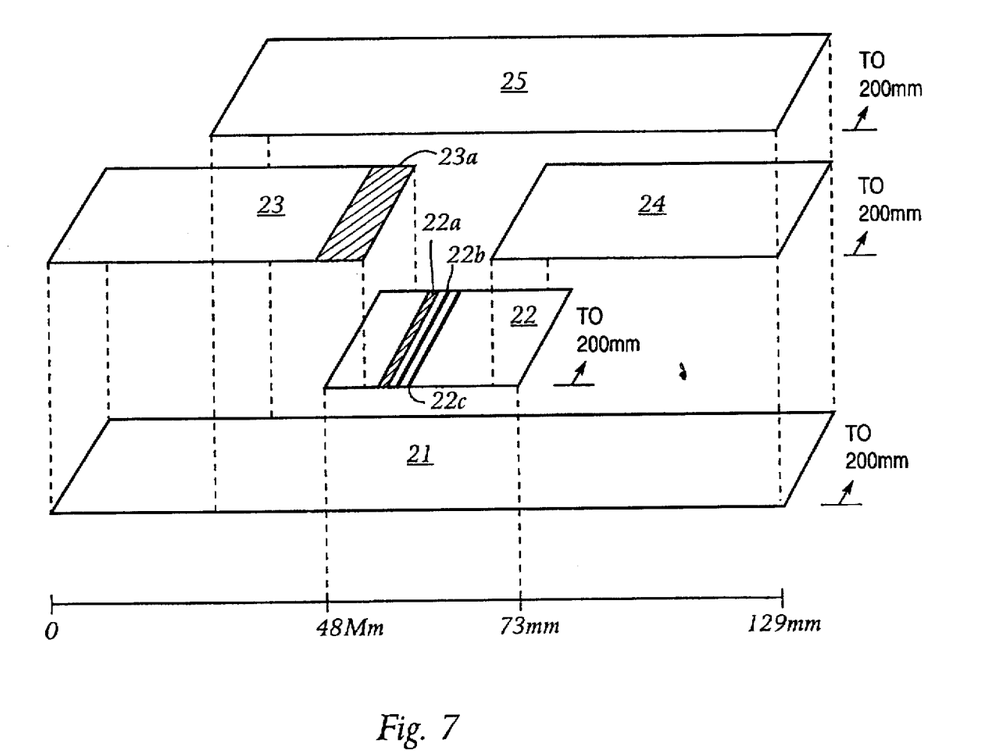
FIG. 7 illustrates the assembly of the device.

Referring to FIG. 7, a sheet of white vinyl (129 mm×200 mm, FIG. 7; 21) is placed on a flat surface. The cover paper on the white vinyl sheet is removed to expose the adhesive. A strip of material (25 mm×200 mm, FIG. 7; 22) containing latex and antibody lines (FIG. 7; 22a, 22b, 22c) is attached to the white vinyl sheet. The analyte detection region is placed at a position between the 48 mm and the 73 mm marks on the white vinyl sheet with the latex close to the 48 mm mark. A strip of the sample receiving region (51 mm×200 mm, FIG. 7; 23) is attached to the left edge of the white vinyl sheet with the buffer end (FIG. 7; 23a) of the region overlapped about 3 mm on top of the analyte detection region. The end flow region (59 mm×200 mm, FIG. 7; 24) is attached to the right edge of the white vinyl sheet while overlapping about 3 mm on top of the analyte detection region. The cover paper from the clear mylar sheet is removed (98 mm×200 mm, FIG. 7; 25) to expose the adhesive. Lining up to the right edge, the cover is attached to the clear mylar sheet with the adhesive side down on top of the end flow region, analyte detection region and sample receiving region. The whole sheet is pressed with a roller to ensure the lamination is secure. The laminated sheet is then cut to 6 mm wide sticks.

Procedure for Testing the Presence or Absence of hCG from Liquid Samples

The assay device is placed into the urine stream for at least 5 seconds. The device is then placed on a paper towel. Within one minute, the test result if positive for hCG will appear as one blue line together with one red line. If only a red line appears then the results are negative. The red latex is used as a control to ensure the assay reagents are working and that lateral flow is occurring.

The assay device was used by three pregnant women and three nonpregnant women. The three pregnant women had positive results for pregnancy, i.e., a blue and red line. The three nonpregnant women had negative results for pregnancy, i.e., only a red line.

One skilled in the art will readily appreciate that the present invention is well adapted to carry out the objects and obtain the ends and advantages mentioned as well as those inherent therein. The immunological methods and devices for detecting analytes in biological samples as described herein are presently representative of preferred embodiments, are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

We claim:

1. An immunochromatographic assay device for detection of the presence or absence of an analyte in a liquid sample, wherein said immunochromatographic assay device consists of:

(a) a separate sample receiving region comprising a porous material which conducts lateral flow of a liquid sample, in lateral flow contact with (b) a separate analyte detection region comprising a porous material which conducts lateral flow of said liquid sample, wherein said analyte detection region comprises a first and a second mobile labeling reagent at a discrete labeling situs, an immobile capture reagent at a discrete capture situs, and an immobile control reagent at a discrete control situs, wherein said first labeling reagent is capable of forming a complex with said analyte; said capture reagent is capable of binding said analyte-labeling reagent complex and said control reagent is capable of binding said second labeling reagent, wherein said analyte detection region is in lateral flow contact with (c) a separate end flow region comprising a porous material which conducts lateral flow of said liquid sample and capable of absorbing excess liquid sample, wherein said liquid sample laterally flows from said sample receiving region towards said end flow region, and mixes with said first and second labeling reagents to move said first and second labeling reagents towards said end flow region, wherein the back of said porous materials are laminated with a semi-rigid material of at least 0.005 inches thick to produce a device with adequate mechanical strength, and the front of said porous materials partially covered with a plastic material so as to leave a portion of said sample receiving region exposed for sample application and allow the discrete capture situs and said discrete control situs to be visible.

2. The device of claim 1 wherein said capture reagent is antibody or an immunologically reactive fragment thereof specific for said analyte.

3. The device of claim 1 wherein said first labeling reagent is an antibody or an immunologically reactive fragment thereof specific for said analyte, and said second labeling reagent is not immunologically reactive to said analyte, wherein said first labeling reagent is attached to a first labeling particle and said second labeling reagent is attached to a second labeling particle.

4. The device of claim 1 wherein said porous material is nitrocellulose, nitrocellulose blends with polyester, cellulose, paper or nylon.

5. The device of claim 1 wherein said semi-rigid material is vinyl.

6. The device of claim 1 wherein said plastic material is mylar.

7. The device of claim 1 wherein said control reagent is antibody or an immunologically reactive fragment specific for said second labeling reagent.

8. The device of claim 3 wherein said particles are colored latex, dye sols, colloidal gold or liposomes containing dye.

9. An immunochromatographic assay device for detection of the presence or absence of an analyte in a liquid sample, wherein said immunochromatographic assay device consists of:

(a) a separate sample receiving region comprising a porous material which conducts lateral flow of a liquid sample, wherein said sample receiving region comprises a first and second mobile labeling reagent at a discrete labeling situs, wherein said first labeling reagent is capable of forming a complex with said analyte, wherein said sample receiving region is in lateral flow contact with (b) a separate analyte detection region comprising a porous material which conducts lateral flow of said liquid sample, wherein said material region comprises an immobile capture reagent at a discrete capture situs, and an immobile control reagent at a discrete control situs, wherein said capture reagent is capable of binding said analyte-labeling reagent complex and said control reagent is capable of binding said second labeling reagent, wherein said analyte detection region is in lateral flow contact with (c) a separate end flow region comprising a porous material which conducts lateral flow of said liquid sample and capable of absorbing excess liquid sample, wherein said liquid sample laterally flows from said sample receiving region towards said end flow region, and mixes with said first and second labeling reagents to move said first and second labeling reagents towards said end flow region, wherein the back of said porous materials are laminated with a semi-rigid material of at least 0.005 inches thick to produce a device with adequate mechanical strength, and the front of said porous materials partially covered with a plastic material so as to leave a portion of said sample receiving region exposed for sample application and allow the discrete capture situs and said discrete control situs to be visible.

10. An immunochromatographic assay device for detection of the presence or absence of an analyte in a liquid sample, wherein said immunochromatographic assay device consists of:

(a) a separate sample receiving region comprising a porous material which conducts lateral flow of a liquid sample, in lateral flow contact with (b) a labeling reagent region comprising a first and second mobile labeling reagent, wherein said first labeling reagent is capable of binding said analyte-labeling reagent complex, wherein said labeling reagent region is in lateral flow contact with (c) a separate analyte detection region comprising a porous material which conducts lateral flow of said liquid sample, wherein said separate analyte region comprises an immobile capture reagent at a discrete capture situs, and an immobile control reagent at a discrete control situs, wherein said capture reagent is capable of binding said analyte-labeling reagent complex and said control reagent is capable of binding said second labeling reagent, wherein said analyte detection region is in lateral flow contact with (c) a separate end flow region comprising a porous material which conducts lateral flow of said liquid sample and capable of absorbing excess liquid sample, wherein said liquid sample laterally flows from said sample receiving region towards said end flow region, and mixes with said first and second labeling reagents to move said first and second labeling reagents towards said end flow region, wherein the back of said porous materials are laminated with a semi-rigid material of at least 0.005 inches thick to produce a device with adequate mechanical strength, and the front of said porous materials partially covered with a plastic material so as to leave a portion of said sample receiving region exposed for sample application and allow the discrete capture situs and said discrete control situs to be visible.

11. An immunochromatographic assay device for detection of the presence or absence of an analyte in a liquid sample, wherein said immunochromatographic assay device consists of;

(a) a separate sample receiving region comprising a porous material which conducts lateral flow of a liquid sample, in lateral flow contact with (b) a labeling reagent region comprising a first and second mobile labeling reagent, wherein said first labeling reagent is capable of binding said analyte-labeling reagent complex, wherein said labeling reagent region is in lateral flow contact with (c) a separate analyte detection region comprising a porous material which conducts lateral flow of said liquid sample, wherein said separate analyte region comprises an immobile capture reagent at a discrete capture situs, and an immobile control reagent at a discrete control situs, wherein said capture reagent is capable of binding said analyte-labeling reagent complex and said control reagent is capable of binding said second labeling reagent, wherein said analyte detection region is in lateral flow contact with (c) a separate end flow region comprising a porous material which conducts lateral flow of said liquid sample and capable of absorbing excess liquid sample, wherein said liquid sample laterally flows from said sample receiving region towards said end flow region, and mixes with said first and second labeling reagents to move said first and second labeling reagents towards said end flow region, wherein the back of said porous materials are laminated with a semi-rigid material of at least 0.005 inches thick to produce a device with adequate mechanical strength, and the front of said porous material is partially covered with a plastic material such that the portion covering the sample receiving region has holes or openings to expose the sample to the sample receiving region and allow the discrete capture situs and said discrete control situs to be viewed.

12. A method to determine the presence or absence of analyte in a sample, which method comprises applying said sample to the sample receiving region of the device of claims 1, 9, 10 or 11, so as to permit said sample to flow through the analyte detection region and into the end flow region, and detecting the presence or absence of analyte in the analyte detection region at the discrete capture reagent situs containing the capture reagent capable of binding the analyte-labeling reagent complex or the discrete control situs containing the control reagent capable of binding the labeling reagent.

13. The method of claim 12 wherein said analyte is human chorionic gonadotropin (hCG).

14. The method of claim 13 wherein said first labeling reagent is a monoclonal antibody immunoreactive with the $\beta$-epitope of hCG conjugated to blue latex and said second labeling reagent is BSA conjugated to red latex.

15. The method of claim 14 wherein said capture reagent is a monoclonal antibody immunoreactive with the $\alpha$-epitope of hCG.

16. The method of claim 15 wherein said control reagent is a monoclonal antibody immunoreactive with the BSA-conjugated red latex.

17. The method of claim 12 wherein said detection occurs within one minute of applying the sample.

* * * * *

UNITED STATES PATENT AND TRADEMARK OFFICE
CERTIFICATE OF CORRECTION

PATENT NO. : 5,712,172
DATED : January 27, 1997
INVENTOR(S) : Ching, et. al.

It is certified that error appears in the above-identified patent and that said Letters Patent is hereby corrected as shown below:

Item [22],
On the cover page, delete filing date of "April 18, 1995" and insert --May 18, 1995--

Signed and Sealed this

Fifteenth Day of December, 1998

Attest:

Attesting Officer

BRUCE LEHMAN

Commissioner of Patents and Trademarks